(12) United States Patent
Valoti et al.

(10) Patent No.: US 7,947,662 B2
(45) Date of Patent: May 24, 2011

(54) FOLATES, COMPOSITIONS AND USES THEREOF

(75) Inventors: Ermanno Valoti, Desio (IT); Davide Bianchi, Desio (IT); Marco Valetti, Desio (IT)

(73) Assignee: GNOSIS S.p.A., Milan (IT)

( * ) Notice: Subject to any disclaimer, the term of this patent is extended or adjusted under 35 U.S.C. 154(b) by 426 days.

(21) Appl. No.: 12/034,194

(22) Filed: Feb. 20, 2008

(65) Prior Publication Data
US 2009/0209543 A1 Aug. 20, 2009

(51) Int. Cl.
*A61K 31/7008* (2006.01)
*A61K 31/4985* (2006.01)
*A61K 31/519* (2006.01)
*C07H 5/06* (2006.01)
*C07D 471/04* (2006.01)

(52) U.S. Cl. ........ 514/62; 514/249; 536/18.7; 536/55.2; 544/350

(58) Field of Classification Search ............ None
See application file for complete search history.

(56) References Cited

U.S. PATENT DOCUMENTS

| 6,255,295 | B1 * | 7/2001 | Henderson et al. | 514/54 |
| 2002/0094970 | A1 * | 7/2002 | Roubenoff et al. | 514/52 |
| 2005/0113287 | A1 * | 5/2005 | Nelson | 514/2 |

FOREIGN PATENT DOCUMENTS

| EP | 0 409 125 A | 1/1991 |
| EP | 0 773 221 A1 | 5/1997 |
| FR | 2 137 186 A | 12/1972 |
| WO | WO2008/153945 | * 12/2008 |

OTHER PUBLICATIONS

Djukic, Alexsandra, "Folate-Responsive Neurologic Diseases" Pediatric Neurology (2007) vol. 37 pp. 387-397.*
Hermann et al., "Biomarkers of folate and vitamin B12 status in cerebrospinal fluid" Clin Chem Lab Med (2007) vol. 45 No. 12 pp. 1614-1620.*
Meshkin et al., "Folate Nutrigenetics: A Convergence of Dietary Folate Metabolism, Folic Acid Supplementation, and Folate Antagonist Pharmacogenetics" Drug Metabolism Letters (2007) vol. 1, pp. 55-60.*
Merriam-Webster's Collegiate Dictionary, published 1998 by Merriam-Webster, Incorporated, p. 924.*

* cited by examiner

*Primary Examiner* — Eric S Olson
(74) *Attorney, Agent, or Firm* — Amin Talati, LLC; Janine A. Moderson; George M. Carrera, Jr.

(57) ABSTRACT

The present invention relates to folates, compositions and uses thereof; In particular, this invention describes a crystalline or amorphous compound which is a substituted or unsubstituted folate or a reduced folate, or the natural or unnatural isomers thereof, of at least one organic base, as well as compositions and uses thereof. The compounds of the invention show a long lasting stability as well as a peculiarly high water-solubility.

25 Claims, No Drawings

FOLATES, COMPOSITIONS AND USES THEREOF

The present invention relates to folates, compositions and uses thereof; in particular, this invention describes crystalline and amorphous compounds which are either folates or reduced folates, or the natural or unnatural isomers thereof, of at least one organic base, as well as compositions and uses thereof.

Folic acid, i.e. N-[4-[[(2-amino-1,4-dihydro-4-oxo-6-pteridinyl)methyl]amino]benzoyl]-L-glutamic acid, and folate, the anion thereof, are forms of the water-soluble vitamin B9 and the precursors of dihydrofolic and tetrahydrofolic acids, and of the respective anions thereof. They occur naturally in food, mostly as conjugates thereof, particularly in liver, kidneys, yeast, fruit and leafy green vegetables, and can also be taken as supplements. Commercially available folic acid, as the above mentioned derivatives thereof, are yet prepared synthetically.

Folic acid occurs as a yellow or yellowish-orange crystalline powder and is very slightly soluble in water and insoluble in alcohol; it is readily soluble in dilute solutions of alkali hydroxides and carbonates. Aqueous solutions of folic acid are heat sensitive and rapidly decompose in the presence of light and/or riboflavin; solutions should be therefore stored in a cool place, protected from light.

As it is well known, vitamins of the B-complex group help the body to convert carbohydrates into glucose, which is metabolized to produce energy. These vitamins are essential in the breakdown of fats and proteins and play an important role in maintaining muscle tone along the lining of the digestive tract and promoting health of the nervous system, skin, hair, eyes, mouth and liver.

It is also known that folic acid is necessary for the production and maintenance of new cells. This is especially important during periods of rapid cell division and growth such as infancy and pregnancy. Folate is needed to replicate DNA. Thus folate deficiency hinders DNA synthesis and cell division, affecting most clinically the bone marrow, a site of rapid cell turnover. Because RNA and protein synthesis are not hindered, large red blood cells, i.e. megaloblasts, are produced, resulting in macrocytic anemia, such as megaloblastic anemia (as may be seen in celiac disease) and in anemias of nutritional origin, or in pregnancy, infancy, or childhood. Accordingly, both adults and children need folate to make normal red blood cells and prevent anemia. Folate also helps prevent changes to DNA that may lead to cancer.

It is also known that folic acid derivatives such as diverse tetrahydrofolic acid derivatives can be used as drugs or as basic substance for the preparation of other derivatives. Yet, also tetrahydrofolic acid and the derivatives thereof are known to possess an extreme instability, particularly due to their susceptibility to oxidation.

In particular, 5-methyltetrahydrofolic acid has importance as a drug ingredient mainly in oncology, as concomitant therapy with methotrexate and 5-fluorouracil treatment, and in the treatment of folic acid deficiency anaemia associated with pregnancy, antibiotic therapy etc.

Among folates and reduced folates, the calcium salts can be mentioned as the most relatively stable derivatives: U.S. Pat. No. 5,817,659 and U.S. Pat. No. 6,441,168 disclose crystalline salts, preferably calcium salts, of 5-methyl-(6R,S)-, -(6S)- or -(6R)-tetrahydrofolic acid having a water of crystallization of at least one equivalent per equivalent of said acid. Calcium 5-methyltetrahydrofolate is the only folic acid derivative on the market which is able directly to penetrate the blood/brain barrier without further metabolism. Naturally occurring 5-methyltetrahydrofolic acid is solely in the S form; the R form is biochemically inactive and is excreted through the kidney.

The insolubility in water of these salts has been reported. Besides, a number of compositions for human and animal consumption, comprising either folates and/or reduced folates, are disclosed, in various forms and together with vitamins, arginine, lysine, thiamine and/or other active ingredients, for instance in U.S. Pat. No. 5,817,659, U.S. Pat. No. 5,997,915, U.S. Pat. No. 6,093,703, U.S. Pat. No. 6,241,996, U.S. Pat. No. 6,254,904, U.S. Pat. No. 6,261,600, U.S. Pat. No. 6,271,374, U.S. Pat. No. 6,440,450, U.S. Pat. No. 6,441,168, U.S. Pat. No. 6,444,218, U.S. Pat. No. 6,451,360, U.S. Pat. No. 6,514,973, U.S. Pat. No. 6,544,944, U.S. Pat. No. 6,596,721, U.S. Pat. No. 6,605,646, U.S. Pat. No. 6,673,381 U.S. Pat. No. 6,808,725, U.S. Pat. No. 6,914,073, U.S. Pat. No. 6,921,754, U.S. Pat. No. 6,995,158, US 2002/0094970, US 2004/0219262, US 2005/0113332, US 2006/0063768, either as a nutritional supplement or for the treatment and prevention of various diseases such as, for instance, neurological, pathopsychological, cardiovascular diseases, arthritic and inflammation conditions.

A higher chemical stability together with a desirable water-solubility which would make possible the pharmaceutical use of folates and/or reduced folates and/or the compositions comprising such compounds, without any particular precaution, is therefore still demanded.

It has been unexpectedly found that a long lasting stability as well as a peculiarly high water-solubility can be obtained by the present invention.

Indeed, according to a first aspect, the present invention concerns a crystalline or amorphous compound which is a substituted or unsubstituted folate or a reduced folate, or the natural or unnatural isomers thereof, of at least one organic base selected from the group consisting of D-glucosamine and D-galactosamine.

Preferably, the reduced folate of the present invention shows a (6R,S), (6S) or (6R) configuration and it is, in particular, a di- or tetrahydrofolate.

The folate and the reduced folate of the present invention are preferably selected from the group consisting of D-glucosamine, D-galactosamine, -folate, -dihydrofolate, -tetrahydrofolate, unsubstituted or substituted with a 5-methyl-, 5-formyl-, 10-formyl-, 5,10-methylene-, 5,10-methenyl- moiety, the compound, whenever contemplated, being in a (6R,S), (6S) or a (6R) configuration.

More preferably, the folate and reduced folate of the present invention are selected from the group consisting of D-glucosamine-folate, D-galactosamine-folate, D-glucosamine (6R,S)-tetrahydrofolate, D-glucosamine (6S)-tetrahydrofolate, D-glucosamine (6R)-tetrahydrofolate; D-galactosamine (6R,S)-tetrahydrofolate, D-galactosamine (6S)-tetrahydrofolate, D-galactosamine (6R)-tetrahydrofolate; D-glucosamine 5-methyl-(6R,S)-tetrahydrofolate, D-glucosamine 5-methyl-(6S)-tetrahydrofolate, D-glucosamine 5-methyl-(6R)-tetrahydrofolate; D-galactosamine 5-methyl-(6R,S)-tetrahydrofolate, D-galactosamine 5-methyl-(6S)-tetrahydrofolate, D-galactosamine 5-methyl-(6R)-tetrahydrofolate.

According to a preferred embodiment, the reduced folate of the present invention is in a (6S) configuration. Still more preferably, the folate and the reduced folate are selected from the group consisting of D-glucosamine 5-methyl-(6R,S)-tetrahydrofolate, D-glucosamine 5-methyl-(6S)-tetrahydrofolate, D-glucosamine folate, D-galactosamine 5-methyl-(6R,S)-tetrahydrofolate, D-galactosamine 5-methyl-(6S)-tetrahydrofolate, D-galactosamine folate.

D-glucosamine 5-methyl-(6R,S)-tetrahydrofolate, D-glucosamine 5-methyl-(6S)-tetrahydrofolate and D-glucosamine folate are the most preferred compounds of the present invention.

It is also preferred that the compound of the present invention is in an amorphous state.

Although the term "folate" is generically used in the field to collectively mean a number of chemical forms which are both structurally related and which have similar biological activity to folic acid, it will be generically referred, in the present specification, to a salt of substituted or unsubstituted folic acid and of any natural or non-natural isomers thereof and/or mixtures thereof, whereas the term "reduced folate" will generically refer to a salt of substituted or unsubstituted either dihydrofolic or tetrahydrofolic acid and of any natural or non-natural isomers thereof.

The compound of the invention shows an extraordinary long lasting chemical stability, this actually guaranteeing a purity quite unaltered, even after months, and that the titre of the correspondent folate or reduced folate moiety results substantially unchanged.

Still another peculiarity of the compound of the invention can be seen in that the counter-ion molecule of the folate and reduced folate of the compound of the invention self-evidently shows no toxicity, being already present in animal beings.

Besides to their exceptionally high chemical stability, it can also be noted that the D-glucosamine and D-galactosamine compounds of the present invention show a surprisingly complete solubility in water (even higher than 1 g/ml) which, self-evidently means an excellent bioavailability, adversely to the other folates and reduced folates hitherto known such as, for instance, alkaline and earth-alkaline salts as calcium salts.

According to another aspect, the present invention relates to a composition comprising at least one compound of the present invention.

As the skilled man will understand on the basis of the common general knowledge of the field, the composition of the invention may be formulated in various forms, either solid (f.i. tablets) or liquid (f.i. solutions), preferably in the form of a parenteral and/or oral pharmaceutical preparation, and may further comprise other inactive and/or active ingredients. Among such further ingredients, the composition of the invention may also and preferably comprise at least one of the following substances: lactose monohydrate, microcrystalline cellulose, sodium starch glycolate, stearic acid, vitamins [in particular, vitamin A, B (B1, B2, B6, B12), C, ascorbic acid, ascorbates, D (D3) E, K, PP], arginine, lysine, thiamine, essential, saturated or unsaturated, ω-3 and/or ω-6 fatty acids (preferably DHA, ARA, EPA), SAMe, cobalamin, ubiquinone, probiotics (lactobacilli, spores, yeasts), phospholipids, serine, choline, inositol, ethylendiamine, botanic extracts (blueberry, leucocyanidins, ginkgo biloba, ginseng, green tea, valerian, passion flower, camomile), melatonin, minerals, oligoelements and the like, and may be administered in an effective amount to a subject in the need thereof, depending on the needs and circumstances the case may present.

By mere way of example, the compound and/or the composition of the present invention may be administered in an amount providing for from 5% to 3000%, more preferably 5% to 200% of the subject daily folic acid requirement. In particular, the dose may amount to between 1 and 2,000 µg/day, more preferably to between 1 µg to 500 µg, most preferably to between 20 and 200 µg/day and in particular from 5 µg to 150 µg, per dose unit.

According to another aspect, the present invention discloses the use of at least one compound and/or one composition of the present invention, as above defined, for the preparation of a medicament, a food additive or a nutritional supplement, for the prevention and/or the treatment of either deficiencies or diseases positively affected by the administration of both folates and reduced folates.

By mere way of example, the compound and/or a composition of the present invention, as above defined, may be used for the preparation of a medicament, a food additive or a nutritional supplement, for the prevention and/or the treatment of neurological affection such as, for instance, subacute encephalitis associated with dementia and vacuolar myelopathies; pathopsychological, vascular and cardiovascular such as, for instance premature occlusive arterial disease, severe vascular disease in infancy and childhood, progressive arterial stenosis, intermittent claudication, renovascular hypertension, ischemic cerebrovascular disease, premature retinal artery and retinal vein occlusion, cerebral occlusive arterial disease, occlusive peripheral arterial disease, premature death due to thromboembolic disease and/or ischemic heart disease; autoimmune diseases, such as, for instance, psoriasis, celiac disease, arthritic and inflammation conditions; megaloblastic anaemia due to folate deficiency, intestinal malabsorption, for reducing a female's risk of having a miscarriage and/or of having a fetus with a neural tube defect, a cleft lip defect, and/or a cleft palate defect, for maintaining and/or normalizing the homocysteine level and/or metabolism; alterations of the synthesis and/or the functioning and/or the changes of DNA and RNA and the alterations of cell synthesis; depressive illnesses.

The compound of the invention can be prepared by simply applying the common general knowledge of the field, as the skilled man would easily understand; however, as a non-limitative example, the compound of the invention can be prepared by adding the desired substituted or unsubstituted folic or reduced folic acid to an aqueous solution containing D-glucosamine or D-galactosamine, preferably maintained under nitrogen and stirring, the base being in a molar amount of about 200 to 300% of the acid.

As a consequence, the desired acid results to be entirely dissolved and an homogeneous and clear solution, having a pH between about 6.3 and 8.0 and containing the desired folate or reduced folate, is thereby obtained.

The salts obtained from D-glucosamine or D-galactosamine with desired substituted or unsubstituted folate or reduced folate, in a molar amount of 200%, are completely water-soluble and can be self-evidently collected very easily, as the skilled man would promptly realize, by simply applying the common general knowledge of the field, for instance and alternatively by directly freeze-drying the desired folate or reduced folate solution obtained, or by spray-drying the desired folate or reduced folate solution obtained.

It can be advantageously noted that, regardless of the way of recovering carried out, the desired folate or reduced folate of the present invention is obtained in an approximatively quantitative amount.

The following examples illustrate the invention without limiting it.

EXAMPLE 1

Preparation of D-glucosamine 5-methyl-(6R,S)-tetrahydrofolate 4.60 g (10 mmol) of 5-methyl-(6R,S)-tetrahydrofolic acid were added portion-wise and completely dissolved in 30 ml of an aqueous solution of D-glucosamine (3.58 g, 20 mmol) stirred under nitrogen. The resulting solution (pH 6.53) was freeze-dried, obtaining 8.72 g of the title product.
Analytical Data:
HPLC titre in 5-methyl-(6R,S)-tetrahydrofolic acid: calculated 56.18% (on the dry product); found 55.22% (98.3% of the theoretical value);
Specific rotation $[\alpha]^{20}_D$=+54.2° (C=1 in water)
NMR (D$_2$O): 7.45 (d, 2H); 6.55 (d, 2H); 5.20 (bs, 2H); 4.05 (m, H); 3.70-3.40 (m, 7H); 3.38-3.00 (m, 6H); 2.99-2.70 (m, 4H); 2.40 (s, 3H); 2.15-2.05 (m, 2H); 2.05-1.90 (m, 1H); 1.90-1.75 (m, 1H).

EXAMPLE 2

Preparation of D-glucosamine 5-methyl-(6R,S)-tetrahydrofolate 9.19 g (20 mmol) of 5-methyl-(6R,S)-tetrahydrofolic acid were added portion-wise and completely dissolved in 60 ml of an aqueous solution of D-glucosamine (7.12 g, 40 mmol) stirred under nitrogen. The resulting solution (pH 6.53) was spray-dried, obtaining 16.9 g of the title product.
Analytical Data:
HPLC titre in 5-methyl-(6R,S)-tetrahydrofolic acid: calculated 56.18% (on the dry product); found 55.13 (98.2% of the theoretical value);
Specific rotation $[\alpha]^{20}_D$=+54.0 (C=1 in water)
NMR (D$_2$O): 7.45 (d, 2H); 6.55 (d, 2H); 5.20 (bs, 2H); 4.05 (m, H); 3.70-3.40 (m, 7H); 3.38-3.00 (m, 6H); 2.99-2.70 (m, 4H); 2.40 (s, 3H); 2.15-2.05 (m, 2H); 2.05-1.90 (m, 1H); 1.90-1.75 (m, 1H).

EXAMPLE 3

Preparation of D-glucosamine 5-methyl-(6S)-tetrahydrofolate 4.60 g (10 mmol) of 5-methyl-(6S)-tetrahydrofolic acid, obtained by the resolution of the corresponding (6R,S)-5-methyltetraidrofolic acid, were added portion-wise and completely dissolved in 30 ml of an aqueous solution of D-glucosamine (3.58 g, 20 mmol) stirred under nitrogen. The resulting solution (pH 6.53) was freeze-dried, obtaining 8.72 g of the title product.
Analytical Data:
HPLC titre in 5-methyl-(6S)-tetrahydrofolic acid: calculated 56.18% (on the dry product); found 55.7% (99.1% of the theoretical value);
Specific rotation $[\alpha]^{20}_D$=+42.6° (C=1 in water)
NMR (D$_2$O): 7.45 (d, 2H); 6.55 (d, 2H); 5.20 (bs, 2H); 4.05 (m, H); 3.70-3.40 (m, 7H); 3.38-3.00 (m, 6H); 2.99-2.70 (m, 4H); 2.40 (s, 3H); 2.15-2.05 (m, 2H); 2.05-1.90 (m, 1H); 1.90-1.75 (m, 1H).

EXAMPLE 4

Preparation of D-glucosamine L-folate 4.41 g (10 mmol) of L-folic acid were added portion-wise and completely dissolved in 40 ml of an aqueous solution of D-glucosamine (3.58 g, 20 mmol) stirred under nitrogen. The resulting solution (pH 6.53) was freeze-dried obtaining 7.95 g of the title product.
Analytical Data:
HPLC titre in L-folic acid: calculated 55.2% (on the dry product); found 54.6 (99.0% of the theoretical value);
Specific rotation $[\alpha]^{20}_D$=+44.5° (C=1 in water)
NMR (D$_2$O): 8.42 (s, 1H); 7.45 (d, 2H); 6.42 (d, 2H); 5.20 (bs, 2H); 4.25 (s, 2H); 4.05 (m, 1H); 3.75-3.45 (m, 6H); 3.35-3.20 (m, 2H); 3.15-3.00 (m, 2H); 2.15-2.05 (m, 2H); 2.05-1.90 (m, 1H); 1.90-1.75 (m, 1H).

EXAMPLE 5

Preparation of D-galactosamine 5-methyl-(6R,S)-tetrahydrofolate 4.60 g (10 mmol) of 5-methyl-(6R,S)-tetrahydrofolic acid were added portion-wise and completely dissolved in 30 ml of an aqueous solution of D-galactosamine (3.58 g, 20 mmol) stirred under nitrogen. The resulting solution (pH 6.53) was freeze-dried, obtaining 8.72 g of the title product.
Analytical Data:
HPLC titre in 5-methyl-(6R,S)-tetrahydrofolic acid: calculated 56.18% (on the dry product); found 55.5% (98.8% of the theoretical value);
Specific rotation $[\alpha]^{20}_D$=+51.43° (C=1 in water)
NMR (D$_2$O): 7.45 (d, 2H); 6.55 (d, 2H); 5.20 (bs, 2H); 4.15 (m, H); 3.70-3.35 (m, 7H); 3.30-2.85 (m, 10H); 2.40 (s, 3H); 2.15-2.05 (m, 2H); 2.05-1.90 (m, 1H); 1.90-1.75 (m, 1H).

EXAMPLE 6

Preparation of D-galactosamine 5-methyl-(6S)-tetrahydrofolate 4.60 g (10 mmol) of 5-methyl-(6S)-tetrahydrofolic acid, obtained by the resolution of the corresponding (6R,S)-5-methyltetraidrofolic acid, were added portion-wise and completely dissolved in 30 ml of an aqueous solution of D-galactosamine (3.58 g, 20 mmol) stirred under nitrogen. The resulting solution (pH 6.53) was freeze-dried, obtaining 8.72 g of the title product.
Analytical Data:
HPLC titre in 5-methyl-(6R,S)-tetrahydrofolic acid: calculated 56.18% (on the dry product); found 55.5% (98.8% of the theoretical value);
Specific rotation $[\alpha]^{20}_D$=+66.50 (C=1 in water)
NMR (D$_2$O): 7.45 (d, 2H); 6.55 (d, 2H); 5.20 (bs, 2H); 4.15 (m, H); 3.70-3.35 (m, 7H); 3.30-2.85 (m, 10H); 2.40 (s, 3H); 2.15-2.05 (m, 2H); 2.05-1.90 (m, 1H); 1.90-1.75 (m, 1H).

EXAMPLE 7

Preparation of D-galactosamine L-folate 4.41 g (10 mmol) of L-folic acid were added portion-wise and completely dissolved in 40 ml of an aqueous solution of D-galactosamine (3.58 g, 20 mmol) stirred under nitrogen. The resulting solution (pH 6.53) was freeze-dried obtaining 7.95 g of the title product.
Analytical Data:
HPLC titre in L-folic acid: calculated 55.2% (on the dry product); found 54.7 (99.1% of the theoretical value);
Specific rotation $[\alpha]^{20}_D$=+49.77 (C=1 in water)
NMR (D$_2$O): 8.42 (s, 1H); 7.45 (d, 2H); 6.42 (d, 2H); 5.20 (bs, 2H); 4.25 (s, 2H); 4.05 (m, 1H); 3.75-3.45 (m, 6H); 3.35-3.20 (m, 2H); 3.15-3.00 (m, 2H); 2.15-2.05 (m, 2H); 2.05-1.90 (m, 1H); 1.90-1.75 (m, 1H).

Stability

The stability of the compounds listed in the following table, under powder form and in sealed aluminium foil bag, was tested, keeping the samples in airtight container, protected from light and measuring the purity and the titre thereof after 6 and 12 months.

| Compound | Starting values | | After 6 months | | After 12 months | |
|---|---|---|---|---|---|---|
| | Purity | Titre | Purity | Titre | Purity | Titre |
| D-GLU folate | 99.1 | 54.6 | 98.8 | 54.3 | 98.7 | 54.0 |
| D-GAL folate | 99.2 | 54.8 | 99.1 | 54.5 | 98.7 | 54.2 |
| D-GLU 5-MTHF | 99.1 | 55.2 | 98.9 | 55.0 | 99.0 | 54.8 |
| D-GLU (6S)-5-MTHF | 99.3 | 55.7 | 99.0 | 55.4 | 98.5 | 55.1 |
| D-GAL (6R,S)-5-MTHF | 99.1 | 55.5 | 98.9 | 55.2 | 98.7 | 55.3 |

D-GLU = D-glucosamine;
D-GAL = D-galactosamine

As a comparison, it can be noted that crystalline (6R,S)-, (6S)- and (6R)-tetrahydrofolic acid calcium salts, as disclosed in U.S. Pat. No. 5,817,659 (Example 1), showed a titre decrease of about 2%, after nine months whereas the such decrease, as reported in U.S. Pat. No. 6,271,374 (Example 1) for crystalline (6S)- and (6R)-tetrahydrofolic acid calcium salts, amounts to about 7% after twelve months. As to crystalline 5-methyl-(6S)-tetrahydrofolic acid calcium salts, U.S. Pat. No. 6,441,168 (Example 1) reports instead a titre decrease amounting to about 1% after twelve months.

In view of the data illustrated in the table above, an expiration date of twelve months can be safely established for the compound of the present invention, further noting a titre decrease lower than 1% after twelve months. Any of the compounds listed in the above table showed a high stability since both their purity and titre, even after twelve months, resulted to fall well within the required specifications. In particular, the stability of the acid moiety was observed by HPLC, detecting the purity and titre thereof.

Bioavailability

The biological tests were carried out on 12 mice weighing 200-300 g, administering to each of them one 3 mg capsule containing the dose of the selected compound, as below reported, dispersed in lactose.

The haematic values of the selected compound were subsequently evaluated after regular time intervals (0, 30, 60, 95, 120 min.).

The following compounds, D-glucosamine folate (60 μg), D-glucosamine [6R,S]5-methyltetrahydrofolate (61 μg), D-glucosamine [6S]5-methyltetrahydrofolate (61 μg), D-galactosamine folate (60 μg), D-galactosamine [6R,S]5-methyltetrahydrofolate (61 μg), D-galactosamine [6S]5-methyltetrahydrofolate (61 μg), were tested and compared to the following ones, amorphous folic acid calcium salt (38 μg), amorphous [6R,S]5-methyltetrahydrofolic acid calcium salt (39 μg), amorphous [6S]-5-methyltetrahydrofolic acid calcium salt (39 μg), crystalline folic acid calcium salt (39 μg), crystalline [6R,S]-5-methyltetrahydrofolic acid calcium salt (39 μg), crystalline [6S]-5-methyltetrahydrofolic acid calcium salt (39 μg).

The biological tests showed that, by administering the compounds of the present invention, the haematic levels resulted about 20% higher than the values found administering to the animals an analogous dose of the corresponding folate and reduced folate calcium salts.

Further, it has been noted a slight and yet significant increase of the bioavailability (about 10%) by administering amorphous calcium salts in comparison with crystalline calcium salts, as illustrated in the following table.

| time (h) | D-Glu F (amorphous) (nmol/l) | D-Glu 5-MTHF (amorphous) (nmol/l) | D-Glu (6S)-5-MTHF (amorphous) (nmol/l) | Ca 5-MTHF (crystalline) (nmol/l) (comparative) | Ca 5-MTHF (amorphous) (nmol/l) (comparative) |
|---|---|---|---|---|---|
| 0.5 | 75.3 ± 4.3 | 83.2 ± 4.9 | 83.7 ± 5.2 | 63.2 ± 4.5 | 68.2 ± 5.1 |
| 1 | 79.8 ± 5.2 | 86.,5 ± 4.9 | 86.1 ± 5.0 | 69.0 ± 6.1 | 73.2 ± 5.9 |
| 1.5 | 78.4 ± 4.3 | 83.8 ± 4.3 | 83.7 ± 4.3 | 70.5 ± 4.3 | 75.2 ± 4.3 |
| 2 | 76.8 ± 4.3 | 82.8 ± 4.3 | 83 ± 4.3 | 70.1 ± 4.3 | 74.1 ± 4.3 |

D-Glu = D-glucosamine;
D-Gal = D-galactosamine;
F = folate

It is therefore evident how the high water-solubility of the D-glucosamine and D-galactosamine compounds of the present invention positively and significantly affects the absorption thereof, thus enhancing the bioavailability of all the molecule active moieties.

The invention claimed is:

1. A crystalline or amorphous solid compound which is a folic acid salt comprising: a moiety selected from D-glucosamine or D-galactosamine, and a folate or a reduced folate moiety selected from the group consisting of -folate, -dihydrofolate, and -tetrahydrofolate, wherein the folate or reduced folate moiety is unsubstituted or substituted with a moiety selected from the group consisting of 5-methyl-, 5-formyl-, 10-formyl-, 5,10-methylene-, and 5,10-methenyl, the compound, whenever contemplated, being in a (6R,S), (6S) or a (6R) configuration, or a salt thereof.

2. The compound according to claim 1, selected from the group consisting of D-glucosamine-folate, D-galactosamine-folate, D-glucosamine (6R,S)-tetrahydrofolate, D-glucosamine (6S)-tetrahydrofolate, D-glucosamine (6R)-tetrahydrofolate, D-galactosamine (6R,S)-tetrahydrofolate, D-galactosamine (6S)-tetrahydrofolate, D-galactosamine (6R)-tetrahydrofolate, D-glucosamine 5-methyl-(6R,S)-tetrahydrofolate, D-glucosamine 5-methyl-(6S)-tetrahydrofolate, D-glucosamine 5-methyl-(6R)-tetrahydrofolate, D-galactosamine 5-methyl-(6R,S)-tetrahydrofolate, D-galactosamine 5-methyl-(6S)-tetrahydrofolate, D-galactosamine 5-methyl-(6R)-tetrahydrofolate, and salts thereof.

3. The compound according to claim 1, selected from the group consisting of D-glucosamine 5-methyl-(6R,S)-tetrahydrofolate, D-glucosamine 5-methyl-(6S)-tetrahydrofolate, D-glucosamine-folate, D-galactosamine 5-methyl-(6R,S)-tetrahydrofolate, D-galactosamine 5-methyl-(6S)-tetrahydrofolate, D-galactosamine-folate, and salts thereof.

4. The compound according to claim 1, which is D-glucosamine 5-methyl-(6R,S)-tetrahydrofolate or D-glucosamine 5-methyl-(6S)-tetrahydrofolate, or a salt thereof.

5. The compound according to claim 1, which is D-glucosamine folate, or a salt thereof.

6. The compound according to claim 1, wherein the reduced folate is in a (6S) configuration.

7. The compound according to claim 1, which is in an amorphous state.

8. The compound according to claim 7, wherein the reduced folate is D-glucosamine 5-methyl-(6S)-tetrahydrofolate or D-galactosamine 5-methyl-(6S)-tetrahydrofolate, or a salt thereof.

9. The compound according to claim 8, which is D-glucosamine 5-methyl-(6S)-tetrahydrofolate, or a salt thereof.

10. A composition comprising at least one compound according to claim 1.

11. The composition according to claim 10, wherein the at least one compound is a crystalline or amorphous compound which is a substituted or unsubstituted folate or a reduced folate, or the natural or unnatural isomers thereof, or a salt thereof, of at least one organic base selected from the group consisting of D-glucosamine and D-galactosamine and wherein it further comprises at least one of the following substances: lactose monohydrate, microcrystalline cellulose, sodium starch glycolate, stearic acid, vitamins, ascorbic acid, ascorbates, arginine, lysine, thiamine, essential, saturated or unsaturated, ω-3 and/or ω-6 fatty acids, S-adenosylmethionine (SAMe), cobalamin, ubiquinone, probiotics, phospholipids, serine, choline, inositol, ethylendiamine, botanic extracts, melatonin, minerals, or oligoelements.

12. The composition according to claim 10, wherein the at least one compound is selected from the group consisting of D-glucosamine-folate, D-galactosamine-folate, D-glucosamine (6R,S)-tetrahydrofolate, D-glucosamine (6S)-tetrahydrofolate, D-glucosamine (6R)-tetrahydrofolate; D-galactosamine (6R,S)-tetrahydrofolate, D-galactosamine (6S)-tetrahydrofolate, D-galactosamine (6R)-tetrahydrofolate; D-glucosamine 5-methyl-(6R,S)-tetrahydrofolate, D-glucosamine 5-methyl-(6S)-tetrahydrofolate, D-glucosamine 5-methyl-(6R)-tetrahydrofolate; D-galactosamine 5-methyl-(6R,S)-tetrahydrofolate, D-galactosamine 5-methyl-(6S)-tetrahydrofolate, D-galactosamine 5-methyl-(6R)-tetrahydrofolate, and salts thereof.

13. The composition according to claim 10, wherein the at least one compound is selected from the group consisting of D-glucosamine 5-methyl-(6R,S)-tetrahydrofolate, D-glucosamine 5-methyl-(6S)-tetrahydrofolate, D-glucosamine-folate, D-galactosamine 5-methyl-(6R,S)-tetrahydrofolate, D-galactosamine 5-methyl-(6S)-tetrahydrofolate, D-galactosamine-folate, and salts thereof.

14. The composition according to claim 10, wherein the at least one compound is D-glucosamine 5-methyl-(6R,S)-tetrahydrofolate or D-glucosamine 5-methyl-(6S)-tetrahydrofolate, or a salt thereof.

15. The composition according to claim 10, wherein the at least one compound is D-glucosamine folate, or a salt thereof.

16. The composition according to claim 11, wherein when present said vitamin is at least one selected from the group consisting of vitamin A, vitamin B, vitamin C, vitamin D, vitamin E, vitamin K, and vitamin PP; wherein when present said fatty acid is at least one selected from the group consisting of docosahexaenoic acid (DHA), arachidonic acid (ARA), and eicosapentaenoic acid (EPA); wherein when present said probiotics are at least one selected from the group consisting of lactobacilli, a spore, and a yeast; and wherein when present said botanic extract is at least one selected from the group consisting of blueberry, leucocyanidins, ginkgo biloba, ginseng, green tea, valerian, passion flower, and camomile.

17. The composition according to claim 16, wherein vitamin B is selected from the group consisting of vitamin B1, vitamin B2, vitamin B6 and vitamin B12, and wherein vitamin D is vitamin D3.

18. The composition according to claim 11, wherein the at least one compound is selected from the group consisting of D-glucosamine-folate, D-galactosamine-folate, D-glucosamine (6R,S)-tetrahydrofolate, D-glucosamine (6S)-tetrahydrofolate, D-glucosamine (6R)-tetrahydrofolate; D-galactosamine (6R,S)-tetrahydrofolate, D-galactosamine (6S)-tetrahydrofolate, D-galactosamine (6R)-tetrahydrofolate; D-glucosamine 5-methyl-(6R,S)-tetrahydrofolate, D-glucosamine 5-methyl-(6S)-tetrahydrofolate, D-glucosamine 5-methyl-(6R)-tetrahydrofolate; D-galactosamine 5-methyl-(6R,S)-tetrahydrofolate, D-galactosamine 5-methyl-(6S)-tetrahydrofolate, D-galactosamine 5-methyl-(6R)-tetrahydrofolate, and salts thereof.

19. The composition according to claim 11, wherein the at least one compound is selected from the group consisting of D-glucosamine 5-methyl-(6R,S)-tetrahydrofolate, D-glucosamine 5-methyl-(6S)-tetrahydrofolate, D-glucosamine-folate, D-galactosamine 5-methyl-(6R,S)-tetrahydrofolate, D-galactosamine 5-methyl-(6S)-tetrahydrofolate, D-galactosamine-folate, and salts thereof.

20. The composition according to claim 11, wherein the at least one compound is D-glucosamine 5-methyl-(6R,S)-tetrahydrofolate or D-glucosamine 5-methyl-(6S)-tetrahydrofolate, or a salt thereof.

21. The composition according to claim 11, wherein the at least one compound is D-glucosamine folate, or a salt thereof.

22. A method of treating a deficiency or disease positively affected by the administration of both folates and reduced folates selected from the group consisting of subacute encephalitis associated with dementia, vacuolar myelopathy, premature occlusive arterial disease, severe vascular disease in infancy, severe vascular disease in childhood, progressive arterial stenosis, intermittent claudication, renovascular hypertension, ischemic cerebrovascular disease, premature retinal artery occlusion, premature retinal vein occlusion, cerebral occlusive arterial disease, occlusive peripheral arterial disease, premature death due to thromboembolic disease, premature death due to ischemic heart disease, psoriasis, celiac disease, arthritic condition, inflammation conditions, megaloblastic anaemia due to folate deficiency, intestinal malabsorption, and depressive illness, said method comprising administering to a subject in need thereof an effective amount of the compound according to claim 1.

23. A method of reducing a female's risk of having a miscarriage, reducing a female's risk of having a fetus with a neural tube defect, reducing a female's risk of having a fetus with a cleft lip defect, reducing a female's risk of having a fetus with a cleft palate defect, said method comprising administering to a subject in need thereof an effective amount of a crystalline or amorphous compound which is a folic acid salt comprising: a moiety selected from D-glucosamine or D-galactosamine, and a folate or a reduced folate moiety selected from the group consisting of -folate, -dihydrofolate, and -tetrahydrofolate, wherein the folate or reduced folate moiety is unsubstituted or substituted with a moiety selected from the group consisting of 5-methyl-, 5-formyl-, 10-formyl-, 5,10-methylene-, and 5,10-methenyl-, the compound, whenever contemplated, being in a (6R,S), (6S) or a (6R) configuration, or a salt thereof.

24. A method for maintaining and/or normalizing the homocysteine level and/or metabolism, said method comprising administering to a subject in need thereof an effective amount of the compound according to claim 1.

25. A method of alterating of the synthesis and/or the functioning and/or the changes of DNA and RNA and the alterations of cell synthesis, said method comprising administering to a subject in need thereof an effective amount of the compound according to claim 1.

* * * * *